US012687475B2

(12) United States Patent
Wiebenga et al.

(10) Patent No.: US 12,687,475 B2
(45) Date of Patent: Jul. 21, 2026

(54) SYSTEM AND METHOD FOR QUANTITATIVELY MEASURING GASES GENERATED BY A BATTERY CELL OR BATTERY CELL COMPONENT AS A FUNCTION OF TIME DURING TESTING

(71) Applicant: GM GLOBAL TECHNOLOGY OPERATIONS LLC, Detroit, MI (US)

(72) Inventors: Michelle H. Wiebenga, Farmington Hills, MI (US); Vamakshi Yadav, Sterling Heights, MI (US); Lei Wang, Rochester Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 281 days.

(21) Appl. No.: 18/535,583

(22) Filed: Dec. 11, 2023

(65) Prior Publication Data

US 2025/0189421 A1 Jun. 12, 2025

(51) Int. Cl.
    G01N 7/16 (2006.01)
    G01N 1/44 (2006.01)
    G01N 27/62 (2021.01)
    G01N 33/00 (2006.01)
    (Continued)

(52) U.S. Cl.
    CPC ................. G01N 7/16 (2013.01); G01N 1/44 (2013.01); G01N 27/62 (2013.01); G01N 33/004 (2013.01);
    (Continued)

(58) Field of Classification Search
    CPC .. H01M 50/394; H01M 10/4285; G01N 7/16; G01N 27/62; G01N 1/44; G01N 33/0004;
    (Continued)

(56) References Cited

U.S. PATENT DOCUMENTS

2020/0256921 A1* 8/2020 Hwang ................... G01N 1/24
2020/0350638 A1* 11/2020 Hwang ............... H01M 50/317
(Continued)

FOREIGN PATENT DOCUMENTS

KR 101728495 B1 * 4/2017 ........... H01M 10/48
KR 102676976 B1 * 6/2024 ............. G01D 21/02

OTHER PUBLICATIONS

Geng "High accuracy in-situ direct gas analysis of Li-ion batteries, Journal of Power Sources", vol. 466, 2020, 228211, ISSN 0378-7753 (Year: 2020).*

(Continued)

*Primary Examiner* — Peter J Macchiarolo
*Assistant Examiner* — Monica S Young

(57) ABSTRACT

A method for measuring gases generated by at least a portion of a battery cell includes arranging a test sample in a chamber. The test sample comprises one of a battery cell including terminals and a gas port and a test fixture including terminals and a gas port and housing at least a portion of a battery cell. The method includes connecting the gas port of the test sample to a node; supplying a carrier gas at a known pressure and flow rate to the node; sampling gas at or downstream from the node using at least one of a mass spectrometer and a gas analyzer; and determining concentrations of gases in the test sample using the at least one of the mass spectrometer and the gas analyzer.

20 Claims, 5 Drawing Sheets

(51) Int. Cl.

| | |
|---|---|
| *G01R 1/02* | (2006.01) |
| *G01R 1/04* | (2006.01) |
| *G01R 31/36* | (2020.01) |
| *G01R 31/367* | (2019.01) |
| *G01R 31/382* | (2019.01) |
| *H01M 10/42* | (2006.01) |
| *H01M 50/30* | (2021.01) |

(52) U.S. Cl.
CPC ............. *G01R 1/02* (2013.01); *G01R 1/0408* (2013.01); *G01R 31/36* (2013.01); *G01R 31/367* (2019.01); *G01R 31/382* (2019.01); *H01M 10/4285* (2013.01); *H01M 50/394* (2021.01); *Y02E 60/10* (2013.01)

(58) Field of Classification Search
CPC .............. G01R 31/385; G01R 31/3842; G01R 31/367; G01R 31/382; G01R 1/02; G01R 1/0408; G01R 31/36; Y02E 60/10
USPC ........................................................ 73/31.04
See application file for complete search history.

(56) References Cited

U.S. PATENT DOCUMENTS

| | | | | |
|---|---|---|---|---|
| 2023/0253632 A1* | 8/2023 | Cohen | ............... | H01M 10/4285 |
| | | | | 429/9 |
| 2023/0253633 A1* | 8/2023 | Cohen | ............... | H01M 10/4228 |
| | | | | 429/90 |
| 2023/0275247 A1* | 8/2023 | Lu | .......................... | H01M 8/188 |
| | | | | 429/499 |
| 2024/0283033 A1* | 8/2024 | Sekol | .................... | H01M 10/44 |
| 2024/0387883 A1* | 11/2024 | Gonin | ................... | G01M 3/202 |

OTHER PUBLICATIONS

Translation_KR101728495 MIN (Year: 2017).*
Translation_KR_102676976 (Year: 2024).*
Geng, et al., High accuracy in-situ direct gas analysis of Li-ion batteries, Journal of Power Sources 466 (2020) 228211.

* cited by examiner

SYSTEM AND METHOD FOR QUANTITATIVELY MEASURING GASES GENERATED BY A BATTERY CELL OR BATTERY CELL COMPONENT AS A FUNCTION OF TIME DURING TESTING

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to battery cells, and more particularly to systems and methods for qualitatively measuring battery cell gases during operation and/or heating of the battery cells.

Electric vehicles (EVs) such as battery electric vehicles (BEVs), hybrid vehicles, and/or fuel cell vehicles include one or more electric machines and a battery system including one or more battery cells, modules, and/or packs. A power control system is used to control charging and/or discharging of the battery system during charging and/or driving.

The battery cells include an enclosure housing enclosing a battery cell stack including one or more cathode electrodes, anode electrodes, and separators and electrolyte. The cathode electrodes include a cathode active material layer arranged on a cathode current collector. The anode electrodes include an anode active material layer arranged on an anode current collector.

When the battery cell is exposed to certain conditions such as formation cycling, overcharge or elevated temperature, reactions occur within the battery cell that generate gases. Since the battery cell stack is located inside a sealed enclosure, it is difficult to determine the types of gases that are generated, the concentrations of the gases, and/or the timing of the gases that are generated.

SUMMARY

A method for measuring gases generated by at least a portion of a battery cell includes arranging a test sample in a chamber. The test sample comprises one of a battery cell including terminals and a gas port and a test fixture including terminals and a gas port and housing at least a portion of a battery cell. The method includes connecting the gas port of the test sample to a node; supplying a carrier gas at a known pressure and flow rate to the node; sampling gas at or downstream from the node using at least one of a mass spectrometer and a gas analyzer; and determining concentrations of gases in the test sample using the at least one of the mass spectrometer and the gas analyzer.

In other features, a check valve includes a first port connected to the battery cell and a second port connected to the node. The carrier gas is supplied at a first flow rate that is greater than or equal to ten times a second flow rate of gases produced by the test sample during testing.

The carrier gas comprises a mixture of an inert gas and a reference gas with a predetermined concentration.

In other features, the at least one of the mass spectrometer and the gas analyzer comprises the mass spectrometer. The mass spectrometer is calibrated with the reference gas as an internal standard. The test sample is heated to a predetermined temperature during testing. The test sample is heated based on a temperature profile as a function of time during testing.

In other features, the method includes charging the test sample to a predetermined voltage prior to testing. The method includes at least one of supplying current to and drawing current from the test sample during testing. The method includes sampling a voltage of the battery cell as a function of time during testing.

In other features, the method includes connecting the mass spectrometer to the node using a capillary. The method includes purging the chamber during testing using a purge gas. The method includes monitoring at least one of a chamber temperature, a battery cell temperature, a battery cell pressure, and a chamber pressure as a function of time during testing.

A system for measuring gases in a battery cell includes a chamber including a cavity configured to receive a test sample, wherein the test sample comprises one of a battery cell including terminals and a gas port and a test fixture including terminals and a gas port and housing at least a portion of a battery cell. A check valve includes a first port connected to the gas port of the battery cell and a second port connected to a node. A first gas source supplies a carrier gas to the node including an inert gas and a reference gas having a predetermined concentration. At least one of a mass spectrometer and a gas analyzer configured to sample gas at the node and to determine a concentration of one or more gases in the battery cell as a function of time using the mass spectrometer.

In other features, the carrier gas is supplied at a first flow rate that is greater than or equal to ten times a second flow rate of gases produced by the test sample during testing. The at least one of the mass spectrometer and the gas analyzer comprises the mass spectrometer. The mass spectrometer is calibrated with the reference gas as an internal standard.

In other features, a heater one of heats the test sample to a predetermined temperature during testing, and heats the test sample based on a temperature profile as a function of time during testing.

In other features, a voltage/current sensor/source is configured to at least one of charge the test sample to a predetermined voltage prior to testing, supply current to and drawing current from the test sample during testing, and monitor at least one of current and voltage of the test sample as a function of time during testing.

In other features, the system comprises at least one of a chamber pressure sensor to monitor pressure in the chamber as a function of time during testing and a test sample pressure sensor configured to monitor pressure in one of an enclosure of the battery cell and in the test fixture.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1B:
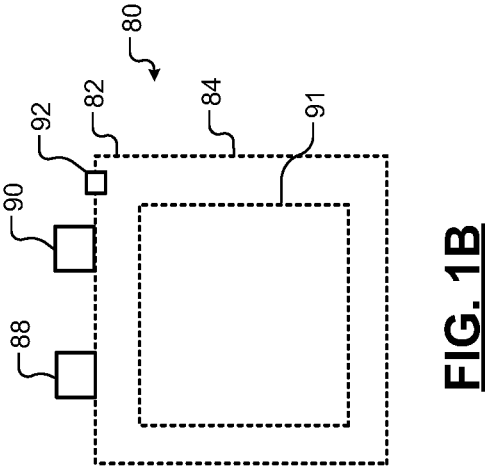
FIG. 1B is a side cross sectional view of a test fixture housing at least a portion of a battery cell according to the present disclosure.

While testing of battery cells according to the present disclosure is described in the context of battery cells for vehicles, the battery cells can be used in other applications such as stationary applications.

The present disclosure relates to a gas testing system and method configured to quantitatively measure gas generated within a test sample including either a battery cell or a test fixture including at least a portion of a battery cell. The test sample can be tested in real time while controlling operating parameters to predetermined operating conditions (e.g., corresponding to heating, formation, and/or cycling).

For example, the test sample can be heated to a predetermined temperature, based on a time-varying temperature profile, or not heated during testing. Gases generated by the test sample are entrained in a carrier gas. In some examples, the carrier gas includes an inert gas and a reference gas with a known or predetermined concentration. The gases from the test sample and the reference gas are sampled by a mass spectrometer and/or a gas analyzer. For example, the mass spectrometer quantitatively measures one or more gases as a function of time during testing using the reference gas concentration as a reference.

In some examples, the battery cell includes a battery cell stack enclosed in a flexible battery enclosure, such as a pouch cell. In other examples, the battery cell includes a battery cell stack enclosed in a prismatic, cylindrical, coin, or other type of battery enclosure made of hard metal with heat resistant seals. In still other examples, one or more sets of cathode electrodes, anode electrodes, and/or separators are arranged in the test fixture that includes a gas port, terminals, and a device for applying pressure to the one or more sets of cathode electrodes, anode electrodes, and/or separators. In still examples, individual or combinations of components of a battery cell, such as anode electrode, cathode electrode, separator, and/or electrolyte may be placed in the test fixture/enclosure. Components may be preconditioned, for example by cycling or charging, then disassembled and reassembled in the test fixture.

In some examples, the mass spectrometer samples the carrier gas and the battery cell gases at a location downstream from the test sample using a mass spectrometer sampling line such as a capillary. The gas mixture including the carrier gas is supplied at a constant flow rate and pressure such that pressure and flow remain nearly constant when gas is generated by the test sample. The precise metering of the reference gas (in the carrier gas) allows the mass spectrometer to quantify other gases sampled from the test sample such as hydrogen, carbon dioxide, ethylene, ethane, methane, or other gases.

The battery testing system allows real time quantitative measurement of the calibrated gases, direct comparison from one test to another, and prevention of electrolyte contamination of the mass spectrometer. For example, gas can be measured from the battery cell in-situ during heating, formation, cycling, and/or other operating conditions that generate gas within the battery cell. While any battery cell format with a gas port can be used, battery cells (or test fixtures) with hard enclosures allow vent gas analysis at higher battery cell temperatures and pressures.

Figure 1A:
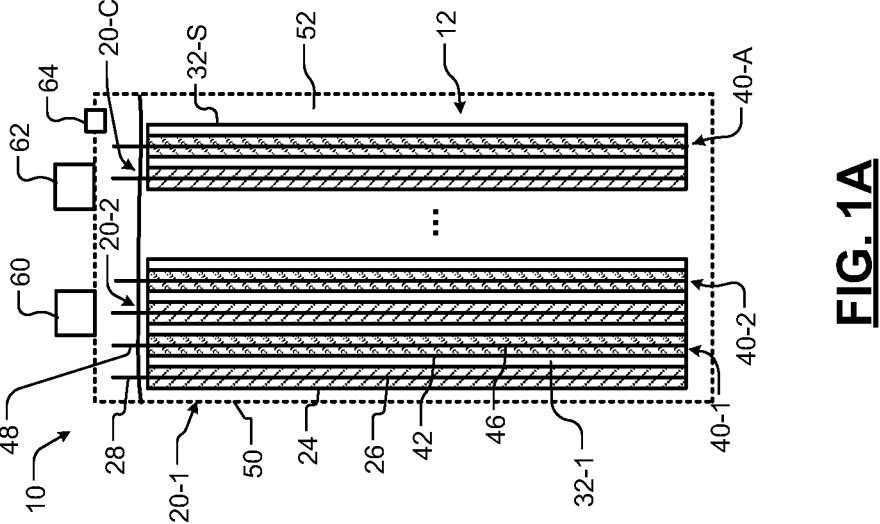
FIG. 1A is a side cross sectional view of an example of a battery cell including a battery cell stack including A anode electrodes, C cathode electrodes, and S separators arranged in a battery enclosure according to the present disclosure.

Referring now to FIG. 1A, a battery cell 10 includes C cathode electrodes 20, A anode electrodes 40, and S separators 32 arranged in a predetermined sequence in a battery cell stack 12, where C, S and A are integers greater than zero. The battery cell stack 12 is arranged in an enclosure 50. The C cathode electrodes 20-1, 20-2, . . . , and 20-C include cathode active material layers 24 arranged on one or both sides of a cathode current collector 26.

The A anode electrodes 40-1, 40-2, . . . , and 40-A include anode active material layers 42 arranged on one or both sides of the anode current collectors 46. In some examples, the A anode electrodes 40 and the C cathode electrodes 20 exchange lithium ions during charging/discharging, although other chemistry may be used. In some examples, one or both of the cathode active material layers 24 and/or the anode active material layers 42 comprise dry coatings including one or more active materials, one or more optional conductive additives, and/or one or more optional binder materials that are applied (e.g., cast, laminated, deposited, etc.) to the current collectors.

In some examples, the cathode current collector 26 and/or the anode current collector 46 comprise metal foil, metal mesh, perforated metal, 3 dimensional (3D) metal foam, and/or expanded metal. In some examples, the current collectors are made of one or more materials selected from a group consisting of copper, stainless steel, brass, bronze, zinc, aluminum, and/or alloys thereof.

External tabs 28 and 48 are connected to the current collectors of the C cathode electrodes 20 and the A anode electrodes 40, respectively, and can be arranged on the same or different sides of the battery cell stack 12. The external tabs 28 and 48 are connected to terminals 60 and 62 of the battery cells. In some examples, the enclosure 50 includes a gas port 64.

In FIG. 1B, a test fixture 80 includes a cover 82 and a bottom portion 84, optional terminals 88 and 90 for providing connections to a portion 91 of a battery cell, and a gas port 92 for sampling gases during testing. In some examples, the portion 91 of the battery cell is arranged in the bottom portion 84 and the cover 82 optionally applies pressure to the portion 91 of the battery cell (or another pressure creating device is used).

Figure 2A:
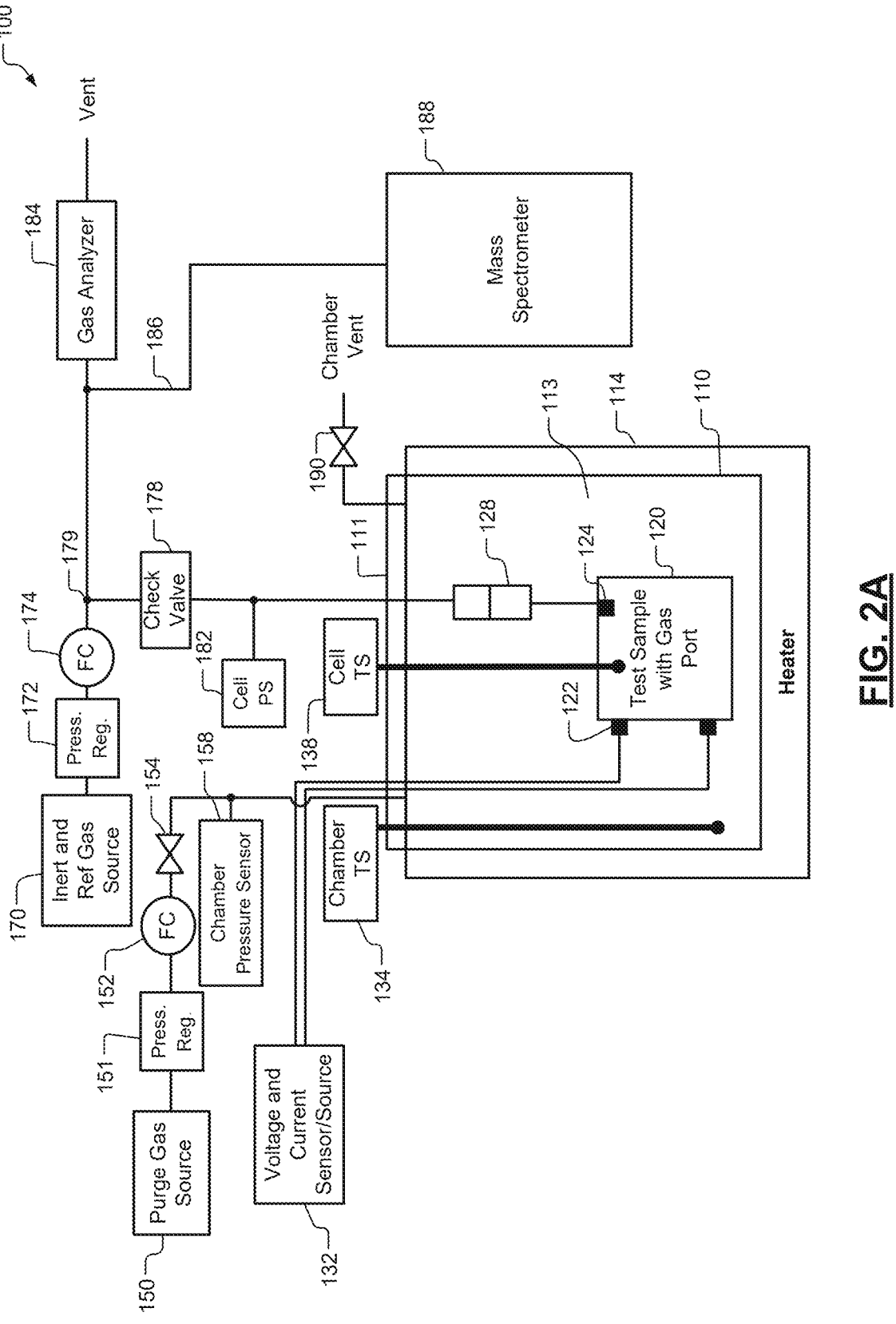
FIGS. 2A and 2B are functional block diagrams and schematics of an example of a gas testing system for a battery cell according to the present disclosure.
Figure 2B:
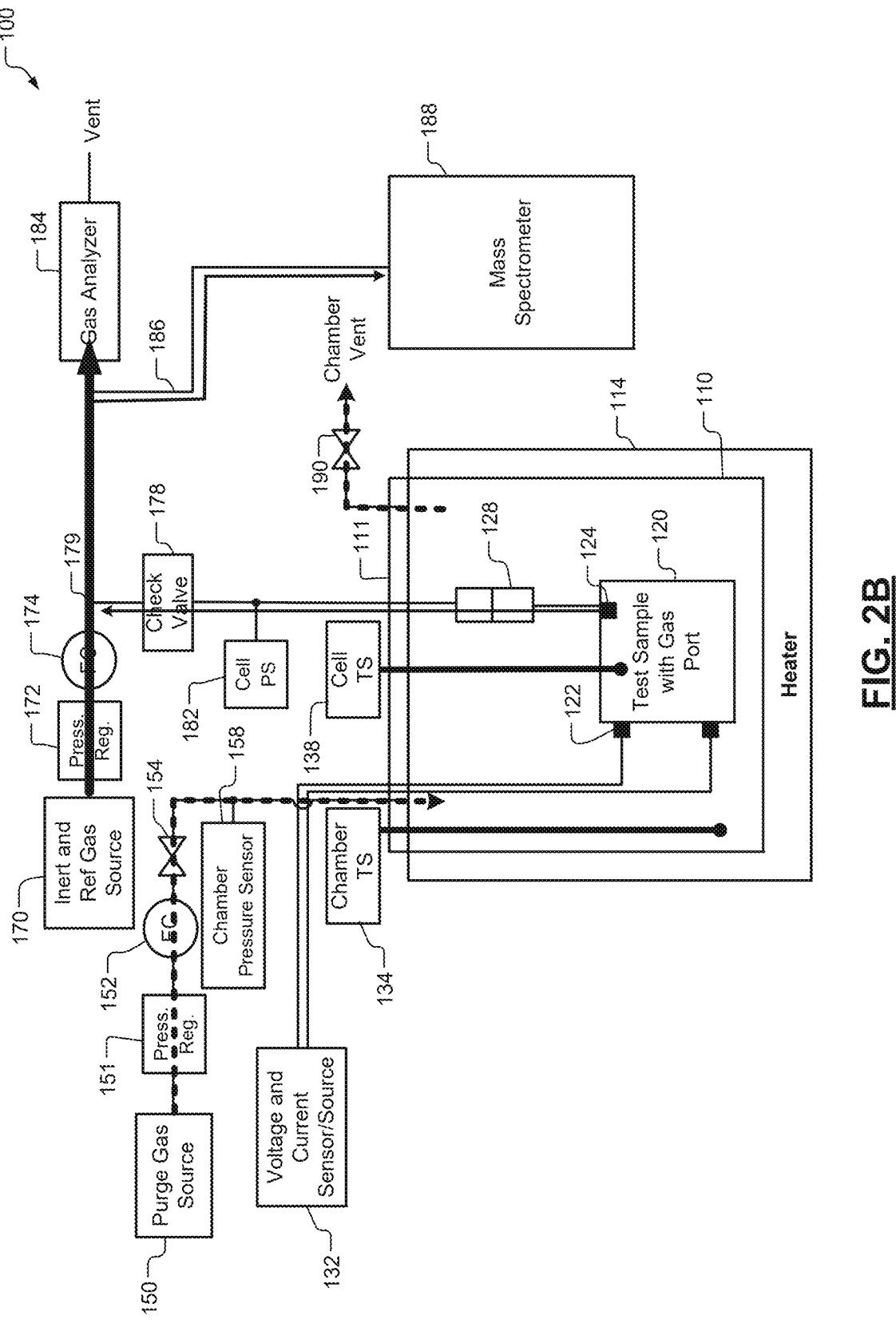

Referring now to FIGS. 2A and 2B, a gas testing system 100 for a battery cell includes a chamber 110 including a cavity 113 enclosed by a lid 111. In FIG. 2A, a heater 114 may be used to control a temperature of the chamber 110 and a test sample 120. A chamber temperature sensor 134 senses a temperature of the chamber 110. A test sample temperature sensor 138 senses a temperature of the test sample 120 (e.g., a battery cell or a test fixture including at least a portion of a battery cell). As can be appreciated, the heater 114 can be controlled in response to feedback from the chamber temperature sensor 134 and/or the test sample temperature sensor 138.

The test sample 120 is arranged inside a cavity of the chamber 110. The test sample 120 includes a gas port 124 and optionally includes positive and negative terminals 122.

In some examples, the gas port 124 may be connected by a gas line to a connector 128 such as a quick disconnect.

A voltage and current sensor/source 132 (e.g., a potentiostat) is connected to the positive and negative terminals 122. The voltage and current sensor/source 132 senses voltage across the positive and negative terminals 122 of the test sample 120 (if used). The voltage and current sensor/source 132 can also apply and/or vary voltage and current across the positive and negative terminals 122 of the test sample 120 as a function of time (or an event or an operating parameter) during testing.

In some examples, a purge gas source 150 supplies purge gas (e.g., an insert gas such as argon (Ar)) via a pressure regulator 151, a flow controller 152, and a gate valve 154 to purge the chamber 110. A gate valve 190 is connected to the chamber 110 to provide a chamber vent to vent the purge gases. A chamber pressure sensor 158 senses pressure within the chamber 110.

In some examples, a check valve 178 is arranged between the test sample 120 and a node 179. In some examples, the check valve 178 opens when a pressure differential between a battery cell side and a sampling side of the check valve 178 is greater than a predetermined pressure differential. In some examples, the predetermined pressure differential is less than or equal to 1 psi (e.g., ⅓ psi).

A gas source 170 supplied carrier gas. In some examples, the carrier gas includes a predetermined mixture of an inert gas and a reference gas is connected by a pressure regulator 172 and the flow controller 174 to the node 179. The node 179 is also connected to a sampling line 186 (e.g., capillary) connected to a vent, a mass spectrometer 188, and an optional gas analyzer 184. In some examples, the gas analyzer 184 comprises a Fourier-transform infrared spectroscopy (FTIR) gas analyzer, a gas chromatography (GC) gas analyzer, a gas sensor such as a hydrogen sensor, and/or a volatile organic compound (VOC) sensor. As can be appreciated, gas sampling can be performed by the mass spectrometer 188 and/or by one or more of the gas analyzers 184.

The mass spectrometer 188 samples the carrier gas (e.g., including the inert and reference gas at a known concentration) from the gas source 170 and gas generated by the test sample (e.g., the battery cell or a portion of a battery cell). The mass spectrometer measures concentrations of gases in the known reference gas and the gases from the battery cell. Examples of sampled gases include molecular hydrogen ($H_2$), carbon dioxide ($CO_2$), methane ($CH_4$), ethane ($C_2H_6$), ethylene ($C_2H_4$), molecular oxygen ($O_2$), carbon monoxide (CO), helium (He), argon (Ar), etc. In some examples, the reference gas includes any gas that is not one of the battery cell gases to be sampled by the mass spectrometer 188. For example, the reference gas can include helium (He). For example, the inert gas can include argon (Ar).

In FIG. 2B, flow of gases during testing are shown. The gas source 170 supplies the known gas mixture at a controlled pressure and flow rate. The reference gas is delivered in the known gas mixture at a predetermined concentration. In some examples, the known gas mixture has a flow rate that is greater than the flow rate of gases produced by the battery cell. In some examples, the flow rate of the known gas mixture is at least 10 times greater than the flow rate of the gases produced by the battery cell. For consistency, the carrier gas flow rate is maintained constant from one battery cell test to another to allow comparison.

Gas from the battery cell is entrained by the known gas mixture. The flow rate of the known gas mixture is significantly greater than the flow rate of gas from the battery cell.

The mass spectrometer 188 uses vacuum to sample a small amount of the known gas mixture and the gas from the battery cell. The purge gas source 150 may be used to evacuate gases from inside of the chamber 110.

Calculation of volumetric flow of each calibrated gas is performed using a volumetric flow of gas (cc/min)=concentration (%)*Carrier gas flow rate (cc/min). Volumetric flow can be integrated to calculate the total volume of each gas generated over a time interval.

Figure 3:
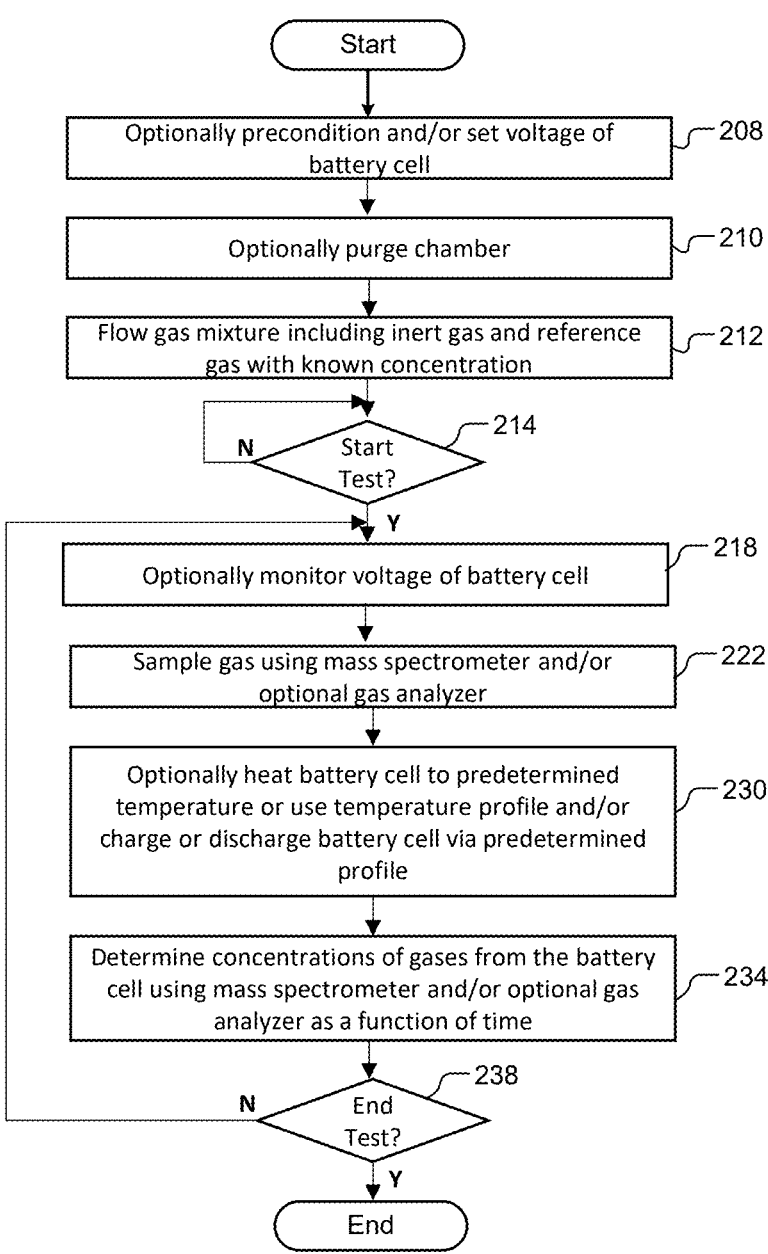
FIG. 3 is a flowchart of an example of a method for operating the gas testing system of FIGS. 2A and 2B according to the present disclosure.

Referring now to FIG. 3, a method for testing a battery cell is shown. At 208, the battery cell is optionally preconditioned and/or a voltage of the battery cell is set to a predetermined voltage. At 210, the chamber is optionally purged. At 212, the gas mixture including an inert gas and a reference gas with a known concentration is supplied.

At 214, the method determines whether the test has started. If 214 is true, the method optionally monitors the voltage of the battery cell. At 222, the gas from the battery cell is optionally sampled using a mass spectrometer and/or a gas analyzer. At 230, the battery is optionally heated to a predetermined temperature, heated based on a temperature profile, and/or charged or discharged using a predetermined charge/discharge profile. At 234, concentrations of gases from the battery cell are determined using the mass spectrometer and/or gas analyzer as a function of time. At 238, the method determines whether the test has ended. If false, the method returns to 218.

Figure 4:
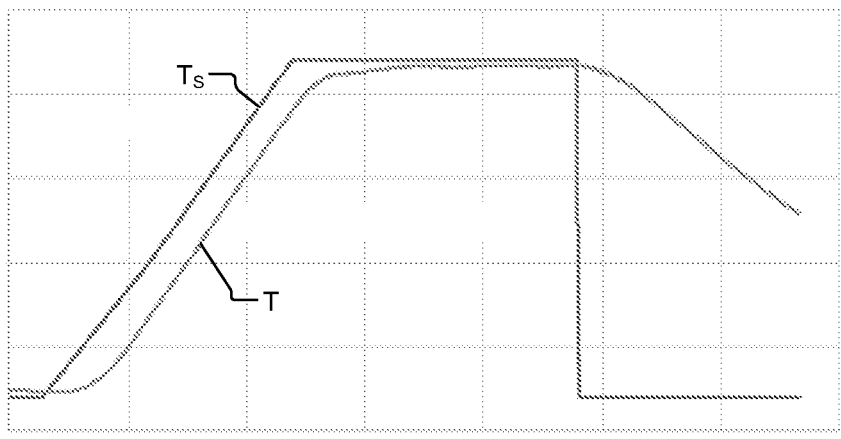
FIG. 4 is a graph illustrating an example of setpoint temperature and battery cell temperature as a function time according to the present disclosure.
Figure 5:
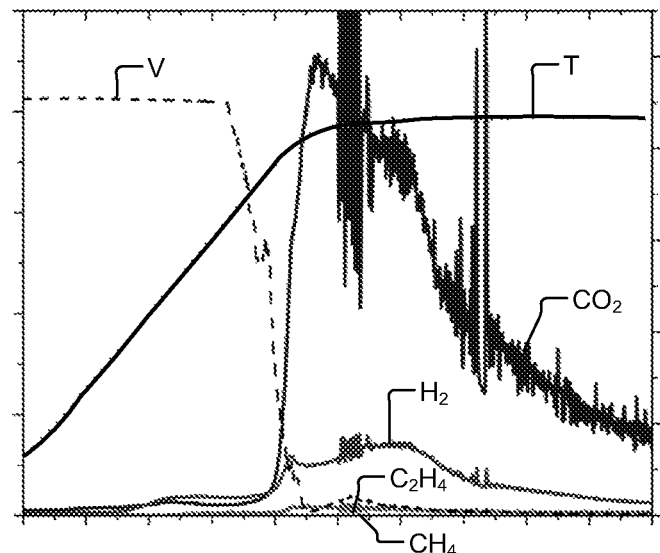
FIG. 5 is a graph illustrating an example of gas concentration percentages, voltage, and cell temperature as a function of time according to the present disclosure.

Referring now to FIGS. 4 and 5, examples of heating and gas concentration data collected during testing of a battery cell is shown. In FIG. 4, a temperature profile of the battery cell under the test is shown. Temperature is increased by the heater based on a setpoint temperature $T_S$ during the test. The temperature of the battery cell T increases in response thereto.

In FIG. 5, the battery cell is initially charged to a predetermined voltage V. As the temperature T of the battery cell increases, the separator melts and causes a short circuit, which causes the voltage to decrease to near zero. Timing and concentrations of various gases (e.g., $CO_2$, $CH_4$, $C_2H_4$, and $H_2$) are detected in real time. For example, as the temperature is raised, the concentration of $CO_2$ increases significantly. The concentration of $H_2$ also increases.

The gas testing system for a battery cell according to the present disclosure quantitatively measures gases generated by the battery cell. The gas testing system uses a battery cell with a gas port that allows gas to pass from the battery cell as pressure builds within the battery cell. The battery cell can include a pouch battery cell or a hard-cased battery cell.

The voltage and current sensor/source (e.g., a potentiostat) monitors cell voltage and/or charges/discharges the battery cell. The optional check valve prevents back flow of carrier gas into the battery cell and avoids electrolyte dry-out. The optional pressure sensor measures the pressure of gas released from the gas port of the battery cell.

When heating is involved, the heater heats the chamber and the battery cell. In some examples, the chamber is flushed with an inert gas (e.g., Ar) to entrain gases/particulates in the case of thermal runaway. Testing of hard-cased battery cells with a gas port is enabled up to a predetermined temperature (e.g., ~300° C.). A temperature sensor such as a thermocouple measures cell temperature.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

What is claimed is:

1. A method for measuring gases generated by at least a portion of a battery cell, comprising:
   arranging a test sample in a chamber,
   wherein the test sample comprises:
     a battery cell including terminals and a gas port; or
     a test fixture including terminals and a gas port, and housing at least a portion of a battery cell;
   connecting the gas port of the test sample to a node via a check valve;
   connecting a gas source to the node via a pressure regulator and a flow controller;
   supplying a carrier gas from the gas source to the node without passing to the chamber, the carrier gas supplied to the node via the pressure regulator and the flow controller at a regulated pressure and flow rate;
   allowing gases produced by the test sample during testing to pass through the check valve when a pressure differential on opposing sides of the check valve is greater than a predetermined pressure differential;
   sampling gas at or downstream from the node using at least one of a mass spectrometer and a gas analyzer, wherein the gas sampled at or downstream from the node includes the carrier gas and the gases produced by the test sample and entrained in the carrier gas; and
   determining concentrations of gases in the test sample using the at least one of the mass spectrometer and the gas analyzer.

2. The method of claim 1, wherein the check valve includes a first port connected to the test sample and a second port connected to the node.

3. The method of claim 1, wherein the carrier gas is supplied at a first flow rate that is greater than or equal to ten times a second flow rate of gases produced by the test sample during testing.

4. The method of claim 1, wherein the carrier gas comprises a mixture of an inert gas and a reference gas with a predetermined concentration.

5. The method of claim 4, wherein:
   the at least one of the mass spectrometer and the gas analyzer comprises the mass spectrometer, and
   the mass spectrometer is calibrated with the reference gas as an internal standard.

6. The method of claim 1, wherein the test sample is heated to a predetermined temperature during testing.

7. The method of claim 1, wherein the test sample is heated based on a temperature profile as a function of time during testing.

8. The method of claim 1, further comprising charging the test sample to a predetermined voltage prior to testing.

9. The method of claim 1, further comprising at least one of supplying current to and drawing current from the test sample during testing.

10. The method of claim 1, further comprising sampling a voltage of the battery cell as a function of time during testing.

11. The method of claim 1, further comprising connecting the mass spectrometer to the node using a capillary.

12. The method of claim 1, further comprising purging the chamber during testing using a purge gas.

13. The method of claim 1, further comprising monitoring at least one of a chamber temperature, a battery cell temperature, a battery cell pressure, and a chamber pressure as a function of time during testing.

14. A system for measuring gases in a battery cell, comprising:
   a chamber including a cavity configured to receive a test sample, wherein the test sample comprises:
     a battery cell including terminals and a gas port; or
     a test fixture including terminals and a gas port, and housing at least a portion of a battery cell;
   a check valve including a first port connected to the gas port of the test sample and a second port connected to a node, the check valve configured to open and allow gases produced by the test sample during testing to pass through when a pressure differential on opposing sides of the check valve is greater than a predetermined pressure differential;
   a first gas source connected to the node via a pressure regulator and a flow controller, the first gas source configured to supply a carrier gas from the gas source to the node without passing to the chamber, the carrier gas supplied to the node via the pressure regulator and the flow controller at a regulated pressure and flow rate, the carrier gas including an inert gas and a reference gas having a predetermined concentration; and
   a mass spectrometer configured to sample gas at the node and to determine a concentration of one or more gases in the battery cell as a function of time, wherein the gas sampled includes the carrier gas and the gases produced by the test sample and entrained in the carrier gas.

15. The system of claim 14, wherein the carrier gas is supplied at a first flow rate that is greater than or equal to ten times a second flow rate of gases produced by the test sample during testing.

16. The system of claim 14, wherein:

the mass spectrometer is calibrated with the reference gas as an internal standard.

17. The system of claim 14, further comprising a heater to one of:

heat the test sample to a predetermined temperature during testing, and heat the test sample based on a temperature profile as a function of time during testing.

18. The system of claim 14, further comprising a voltage/current sensor/source configured to at least one of:

charge the test sample to a predetermined voltage prior to testing;

supply current to and drawing current from the test sample during testing; and monitor at least one of current and voltage of the test sample as a function of time during testing.

19. The system of claim 14, further comprising at least one of:

a chamber pressure sensor to monitor pressure in the chamber as a function of time during testing; and a test sample pressure sensor configured to monitor pressure in one of an enclosure of the battery cell and in the test fixture.

20. The system of claim 14, wherein the mass spectrometer uses vacuum to sample the gas at the node.

\* \* \* \* \*